United States Patent [19]

Uda et al.

[11] Patent Number: 5,171,664
[45] Date of Patent: Dec. 15, 1992

[54] MONOCLONAL ANTIBODY TO OKADAIC ACIDS, PROCESS FOR PRODUCING THE MONOCLONAL ANTIBODY, ASSAY REAGENT FOR ASSAYING OKADAIC ACIDS USING THE MONOCLONAL ANTIBODY, AND ASSAY METHOD

[75] Inventors: Taizo Uda; Yukikatsu Itoh; Takashi Usagawa; Minoru Nishimura; Kasumi Sudoh, all of Ube, Japan

[73] Assignee: UBE Industries, Ltd., Yamaguchi, Japan

[21] Appl. No.: 254,686

[22] Filed: Oct. 7, 1988

[30] Foreign Application Priority Data

Oct. 9, 1987 [JP] Japan .............................. 62-253782
Dec. 15, 1987 [JP] Japan .............................. 62-315380

[51] Int. Cl.$^5$ .................. G01N 33/53; C12Q 1/28; C07K 15/14

[52] U.S. Cl. ..................................... 435/7.9; 435/7.1; 435/21; 435/25; 435/27; 435/28; 435/188; 435/7.92; 435/7.93; 436/548; 530/388.9; 935/110

[58] Field of Search .................. 435/7, 21, 25, 27, 28, 435/188, 7.1, 7.9; 530/387; 436/548; 935/110

[56] References Cited

PUBLICATIONS

Levine, L., et al., Chemical Abstracts, vol. 110, No. 11, Abstract No. 90021Z (1988).
Sevier, E. D., et al., Clin. Chem., vol. 27, No. 11, pp. 1797–1806 (1981).

Primary Examiner—Esther L. Kepplinger
Assistant Examiner—Toni R. Scheiner
Attorney, Agent, or Firm—Wenderoth, Lind & Ponack

[57] ABSTRACT

A monoclonal antibody which specifically binds okadaic acids and a process for producing the monoclonal antibody by culturing a cell strain capable of producing the antibody. The monoclonal antibody to okadaic acids labelled with an enzyme is useful for assaying okadaic acids.

5 Claims, 1 Drawing Sheet

MONOCLONAL ANTIBODY TO OKADAIC ACIDS, PROCESS FOR PRODUCING THE MONOCLONAL ANTIBODY, ASSAY REAGENT FOR ASSAYING OKADAIC ACIDS USING THE MONOCLONAL ANTIBODY, AND ASSAY METHOD

BACKGROUND OF THE INVENTION

This invention relates to a monoclonal antibody to okadaic acids, a process for producing the monoclonal antibody, an assay reagent for assaying okadaic acids using the monoclonal antibody, and an assay method.

Okadaic acids, pectenotoxins and yessotoxin, etc. are known as diarrhetic shellfish poisons found in shellfish such as scallop, mussel, short-necked clam and kotamagai.

In Japan, there have been many cases of poisoning caused by these diarrhetic shellfish poisons. Those which occurred in Iwate Prefecture in 1976, Kanagawa and Miyagi Prefectures in 1977 and Ibaraki and Fukushima Prefectures in 1978 were particularly serious, and several tens to several hundred persons suffered from poisoning at a time.

These happenings led to the need for examining shellfish for the presence of diarrhetic shellfish poisons in amounts which are likely to cause food poisoning.

An immunological assay method using monoclonal antibodies having very high specific reactivity with diarrhetic shellfish poisons (such as okadaic acids, pectenotoxins and yessotoxin) would be an excellent method for solving this problem. The prior art is silent on the preparation of a monoclonal antibody to okadaic acids.

SUMMARY OF THE INVENTION

It is an object of this invention to provide a monoclonal antibody which shows very high specific reactivity with okadaic acids.

Another object of this invention is to provide a process for producing a monoclonal antibody to okadaic acids.

Still another object of this invention is to provide an assay reagent which can assay okadaic acids easily with high sensitivity using a monoclonal antibody to okadaic acids. and to an assay method using the assay reagents.

Further objects of this invention along with its advantages will become apparent from the following description.

According to this invention, the objects and advantages of the invention are firstly achieved by a monoclonal antibody to okadaic acids.

DESCRIPTION OF THE PREFERRED EMBODIMENTS

Figure 1:
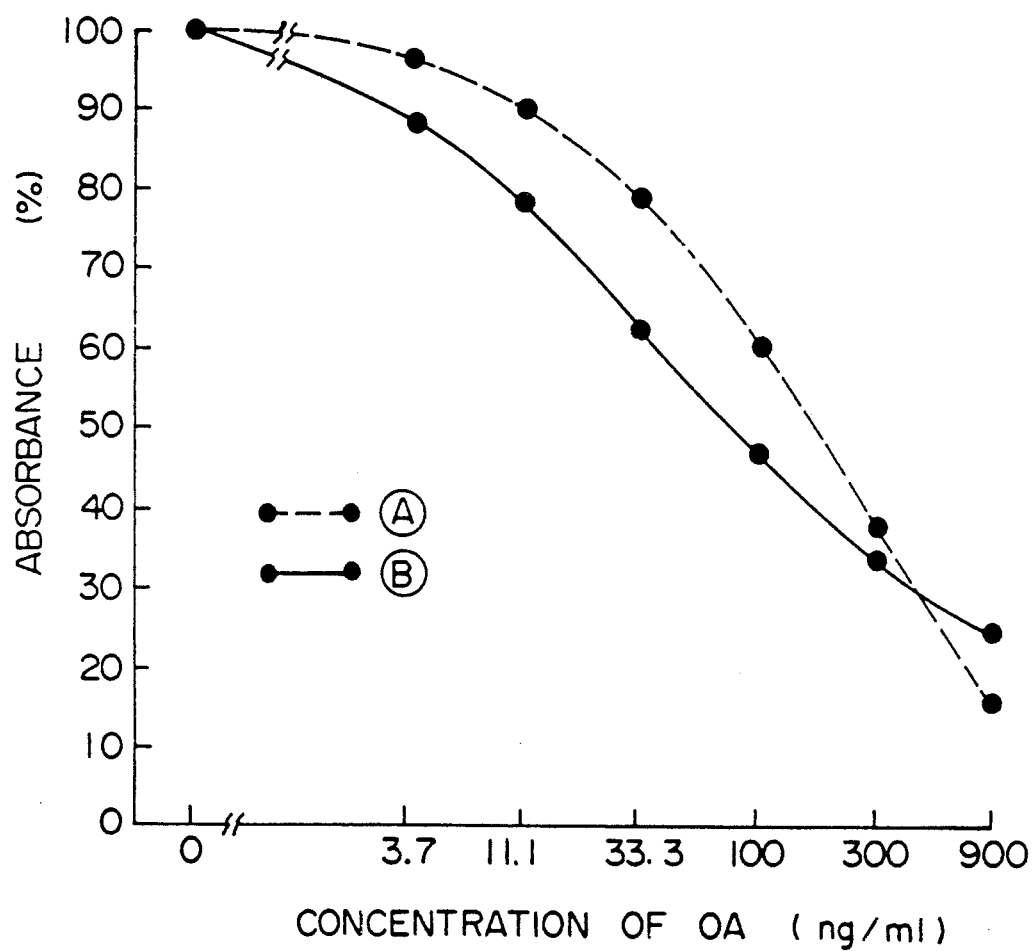
FIG. 1 of the accompanying drawings is a calibration curve showing the relation between the concentration of okadaic acid (OA) and absorbance.

The monoclonal antibody of this invention is produced by a cell strain obtained from an immunized animal and has very high specific reactivity with okadaic acids (OA for short) which are diarrhetic shellfish poisons.

Any immunogens which permit production of monoclonal antibodies having very high specific reactivity with okadaic acids can be used in this invention to immunize animals. Examples are OA, dinophysistoxin-1 ($DTX_1$ for short), dinophysistoxin-3 ($DTX_3$ for short), salts of these, and products obtained by binding them to carriers having a molecular weight of at least 10,000. It is preferred to use these products bound to carriers having a molecular weight of at least 10,000. Examples of the carrier used for this purpose are biopolymers such as bovine serum albumin, ovalbumin, keyhole limpet hemocyanine and immunoglobulins. Animals may be immunized with one or more of these immunogens.

The monoclonal antibody of this invention can be obtained by separating lymphocytes from the immunized animal e.g., a mammal such as a mouse, rat or rabbit), transforming them with a virus, a mutagenic substance, etc., and culturing the transformants. Alternatively, the monoclonal antibody of the invention may be obtained by introducing a DNA having proliferating capacity and thus transforming them (for example, by introducing a DNA precipitated with calcium phosphate, or a DNA obtained by fusion of cells from the same or different kinds of animals), and culturing the transformants. For example, the monoclonal antibody is obtained by fusing lymphocytes obtained from an immunized mouse with mouse myeloma cells, and culturing the resulting hybridoma cells OA-1, OA-2 FERM Deposit No. 1491) or OA-3.

This hybridoma preparation may be carried out in accordance with a known method such as the method of Milstein and Koehler Nature, 256, 495 (1976)]. The outline of a preferred method of preparing such a hybridoma will be described below.

Preparation of a hybridoma capable of producing a monoclonal antibody (1) Preparation of an immunogen and an analytical antigen The immunogen may be prepared, for example, by converting okadaic acids into an active ester using a carbodiimide such as 1-cyclohexyl-3-(2-morpholinoethyl)carbodiimide metho-p-toluenesulfonate (CMEC for short) or 1-ethyl-3-(3-dimethylaminopropyl)carbodiimide, and binding the active ester to a biopolymer such as bovine serum albumin (BSA), ovalbumin (OVA), keyhole limpet hemocyanin (KLH) and gamma-globulin.

The analytical antigen is prepared by repeating the same procedure as in the preparation of the immunogen except that a carrier different from that used in the immunogen preparation is used.

An example of okadaic acids is a compound represented b the following formula

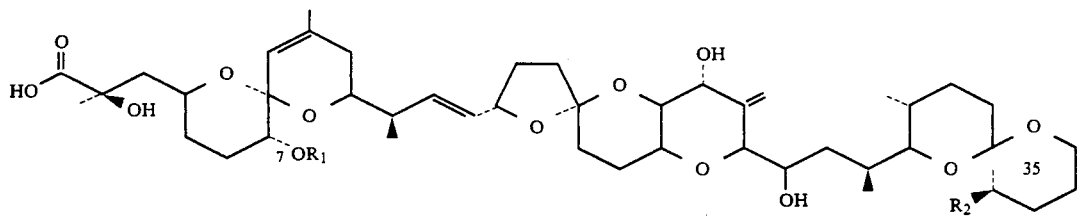

in which $R_1$ represents a hydrogen atom or an acyl group, and $R_2$ represents a hydrogen atom or a methyl group.

A compound of formula (I) in which $R_1$ and $R_2$ are both hydrogen atoms is okadaic acid (OA). A compound of formula I) in which $R_1$ is a hydrogen atom and $R_2$ is a methyl group is $DTX_1$ and a compound of formula (I) in which $R_1$ is an acyl group and $R_2$ is a methyl group is $DTX_3$.

(2) Preparation of lymphocytes of an immunized animal

An animal (such as a mouse or rat) is immunized by administering a solution of the immunogen mentioned in (1) above (1 to 400 micrograms) in PBS (Dulbecco's phosphate buffered saline) to the animal once, or several times with an interval of several weeks.

The first immunization can be carried out without administering an adjuvant (e.g., an immunization promoting subtance including alum, dead tuberclosis bacterial cells, or nucleic acid). Preferably, an emulsion of the immunogen prepared by using an adjuvant is administered.

After determining that the immunized animal has a sufficient antibody titer, the lymphocytes can be obtained from, for example, the blood, lymph node or the spleen several days after the final immunization. For the ease of the experimental operation, it is preferred to obtain them from the spleen.

(3) Preparation of myeloma cells

MPC-11, P3-X63-Ag8.653 653), P3-X63-Ag8-Ul-(P3Ul), P3-NS-1(NS-1 and SP3/0-Ag14(SP2/0) derived from mice and 210.RC Y3.Agl.2.3(Y3) derived from rats can be used for cell fusion. It is preferred however to use myeloma cells which do not produce and secrete an antibody extracellularly, for example 653, P3Ul, NS-1 and SP2/0.

(4) Cell fusion

The cell fusion is carried out by mixing lymphocytes of the immunized animal and the myeloma cells in a ratio of (5-20):1 using a solution for cell suspension not detrimental to the cell fusion, such as a solution of a medium for culturing lymphocytes (such as MEM, DMEM, McCoy, and RPM1 1640) or an isotonic buffer, centrifuging the mixture, and adding a HVJ (Sendai virus) or PEG polyethylene glycol) solution to the resulting pellets (cell mass). The use of the PEG solution is preferred. Particularly preferred is a 30-60% by weight solution of PEG having an average molecular weight of 1000 to 8000. To promote the cell fusion, colchicine, dimethyl sulfoxide or poly-L-arginine, for example, may be used jointly.

The myeloma cells used in the cell fusion may be those derived from an animal different in kind from the immunized animal. In view of the amount of the antibody produced by the resulting hybridoma and the stability of antibody-producing ability, it is preferred to use myeloma cells from the same kind of animal as the immunized one, particularly from an animal of the same strain.

(5) Selection of the hybridoma

Selection of the hybridoma is carried out by culturing the cells after the cell fusion operation in a HAT medium (a medium containing hypoxanthine, aminopterine, thymidine and fetal bovine serum; these components may be those which are generally used for culturing lymphocytes).

Hybridoma cells ar cultured in the wells of a culture plate. The number of the cells is one suitable for screening antibody-forming wells. As required, a substance promoting the proliferation of the hybridoma or cells producing this substance (for example, lymphocytes derived from the thymus, spleen or lymph node) may be used as feeder cells.

The hybridoma selected by proliferating in the HAT medium is cultured for several days in a HT medium (a medium containing hypoxanthine, thymidine and fetal bovine serum; these components may be those generally used in culturing lymphocytes) until the number of the cells reaches one which is suitable for screening antibody-forming wells. Furthermore, the hybridoma cells are cultured in a culture medium containing fetal bovine serum which is generally used for culturing lymphocytes.

(6) Selection of an antibody-producing hybridoma

Whether the hybridoma obtained in (5) produces the desired antibody may be determined by ELISA (enzyme-linked immunosorbent assay), a plaque-forming method, an agglutination reaction method, RIA (a method using a radioisotope), etc. ELISA is preferred.

A procedure of ELISA is, for example, as follows:

The hybridoma culture supernatant is added to each well of an ELISA plate to which the analytical antigen prepared in (1) is fixed. The hybridoma supernatant is then allowed to stand for a fixed period of time. The wells are washed, and an enzyme-labelled antibody which is bound to the washed wells and can react with and bind to an antibody derived from an animal is added to the wells and left to stand for a fixed period of time.

Examples of the enzyme used for labelling are peroxidase, alkaline phosphatase and beta-galactosidase. The antibody to be labelled may be any antibody which can react with, and bind to, only an antibody derived from an animal and bound to the wells. It may be, for example, serum obtained from mice, rats, rabbits or goats, or monoclonal antibodies produced by hydribdoma cells formed by using mouse cells.

The wells are then washed. A substrate solution corresponding to the enzyme used is added and the enzyme activity is measured. It is seen that a hybridoma producing the desired antibody was present in a well which shows enzyme activity.

Thus, hybridoma cells which are recognized to proliferate and produce an antibody can be obtained.

(7) Cloning of the hybridoma

The hybridoma in a well in which antibody production is recognized can be cloned by a limiting dilution method, a single cell manipulation method (one hybridoma cell is added to one well under an inverted microscope), a method by which colonies are picked up using soft agar, or a method using a fluorescent activated cell sorter (FACS). Specifically, the antibody-producing hybridoma selected in (6) is cultured by any of the above cloning methods. Using the supernatants from wells in which the proliferation of the hybridoma is observed, antibody-producing wells were screened by the same ELISA method as used in the selection of the antibody-producing hybridoma in (6). Using the supernatants from the wells in which antibody production is observed, reactivity with other antigens was examined.

The above procedure leads to the selection of hybridoma cells producing a monoclonal antibody having high specificity to okadaic acids and a high antibody titer.

Production of a monoclonal antibody

A monoclonal antibody having high specificity for okadaic acids and a high antibody titer can be produced by culturing the hybridoma cells obtained in (7) in a flask or in the abdominal cavity of an animal.

In the case of culturing in a flask, the hybridoma cells obtained in (7) are cultured in a general medium for lymphocytes culturing containing 0 to 20% fetal bovine serum (such as a medium containing the components of MEM, DMEM, McCoy or RPMI 1640) until the cell density reaches an upper limit. The desired monoclonal antibody is contained in the culture supernatant obtained by a centrifugal operation.

Production of the monoclonal antibody by culturing the hybridoma cells obtained in (7) in the abdominal cavity of an animal may be carried out by using an animal different in kind from the animal from which the cells used in the cell fusion are derived. Preferably, however, the same kind of animal, particularly an animal of the same strain, is used. Specifically, a substance capable of reducing the immunological competence of the animal (e.g., a mineral oil such as pristane) is administered intraperitoneally to a suitable animal such as a mouse, rat or hamster, and several weeks later, the hybridoma cells ($10^6$ to $10^7$) obtained in (7) are intraperitoneally administered, and proliferated to a high density in the abdominal cavity in several weeks. At this time, the monoclonal antibody having high specificity to okadaic acids and a high antibody titer is contained in ascites supernatant obtained by a centrifugal operation. The concentration of the antibody is 10 to 1000 times that in the culture supernatant obtained by culturing in a flask.

The monoclonal antibody obtained by culturing the hybridoma cells in a flask or in the abdominal cavity of an animal is purified by a general protein purification method such as salting out, dialysis, ion-exchange chromatography and affinity chromatography to give a highly pure monoclonal antibody.

Since the monoclonal antibody of the invention obtained as above has very high specific reactivity with okadaic acids, the present invention provides, by utilizing this property of the monoclonal antibody, a reagent for assaying okadaic acids easily with high sensitivity, and an assay method using the monoclonal antibody of the invention.

Thus, according to this invention, there are also provided an assay reagent for okadaic acids, comprising an enzyme-labelled monoclonal antibody to okadaic acids; and a method of assaying okadaic acids which comprises assaying okadaic acids under competitive reaction conditions using an enzyme-labelled monoclonal antibody to okadaic acids.

An enzyme-labelled monoclonal antibody to okadaic acids is novel and within the scope of the present invention.

Examples of the enzyme used in labelling include peroxidase, alkaline phosphatase, beta-galactosidase, catalase, glucose oxidase, lactic acid oxidase, alcohol oxidase and monoamine oxidase. They may be used singly or in combination.

Enzyme labelling of the antibody may be carried out by a known method, for example a one-step method using glutaraldehyde [Immunochemistry, 6, 43 (1969)], a two-step method using glutaraldehyde Immunochemistry, 8, 1175 (]1971)], a periodic acid method Methods in Enzymology, 37, 133 (1975)), or a maleimide method Journal of the Biochemistry, 78, 235 (1975)). The last-mentioned two methods are preferred. The antibody may be directly used for assaying okadaic acids after the enzyme is bound to it. To increase sensitivity further, it is preferred to purify the enzyme-labelled antibody by gel filtration using Sephadex or Sephacryl and use the purified enzyme-labelled antibody as a reagent for assaying okadaic acids. The enzyme-labelled antibody fraction is dialyzed against PBS or Tris-HCl buffer (pH 7.4) lyophilized or filtered through a sterilizing filter, and used as the reagent for assaying okadaic acids.

Okadaic acids may be assayed by this invention by, for example, fixing okadaic acids to a solid-phase support such as a 96-well immunoplate, adding the sample and the assay reagent of this invention together, removing the unreacted materials, adding a substrate solution (the substrate is one corresponding to the enzyme used to label the antibody), and then measuring the absorbance of the color reaction solution.

More specifically, in the assay of okadaic acids, an okadaic acid-high-molecular-weight protein complex is placed on a plate such as a 96-well flatbottomed immunoplate and fixed. The antigen-treated wells were washed and subjected to blocking treatment so that an antibody to okadaic acids does not non-specifically bind to those parts of the wells to which the antigen is not bound. The wells are then washed. Equal volumes of a sample (or a known amount of okadaic acids for preparation of a calibration curve) and the reagent of the invention for assaying okadaic acids are added and left to stand for a fixed period of time. The wells are washed, and a solution of a substrate corresponding to the enzyme used to label the antibody in the okadaic acid assay reagent (containing a substance which forms a color when enzyme reaction takes place) is added to perform enzyme reaction for a fixed period of time. The absorbance of the reaction solution is measured at a wavelength at which the color formed shows a maximum absorbance. A calibration curve is prepared from the results obtained by using a known amount of okadaic acids, and the amount of okadaic acids in the sample can be determined.

In a stage of adding the sample and the okadaic acid assay reagent in the foregoing operating procedure, the assay reagent for okadaic acids competitively reacts with the okadaic acids fixed to the support (antigen for assay okadaic acids) and with the okadaic acids in the sample. As a result, the amount of okadaic acids in the sample can be measured rapidly with high sensitivity.

In addition to the immunoplates, polyethylene beads, polystyrene beads and ABS resin beads may also be used for fixation of okadaic acids.

The following Examples illustrate the present invention specifically. It should be understood that these examples do not limit the scope of the invention.

EXAMPLE 1

Preparation of an immunogen and an antigen for analysis:

An immunogen was prepared by the following procedure.

In 1 ml of 95% dioxane was dissolved 0.5 ml of okadaic acid (OA), and 1.5 mg of N-hydroxysuccinimide and 2.5 mg of 1-cyclohexyl-3-(2-morpholinoethyl)carbodiimide metho-p-toluenesulfonate (CMEC) were added to the solution. The mixture was stirred at room temperature for 3 hours to form OA-N-succinimide ester. The reaction mixture was added to 20 ml of water, and 20 ml of ethyl acetate was added. The mixture was shaken to obtain an ethyl acetate layer. This layer was washed with water, and the solvent was evaporated under reduced pressure to obtain the OA-N-succinimide ester. All the ester was dissolved in 2.5 ml of 0.05M phosphate buffer (pH 7.3), and 2.5 ml of pyridine and 10 mg of ovalbumin (OVA) were added to the solution. The mixture was stirred at 4° C. for 20 hours. The solution was dialyzed against pure water, and a non-dialyzed fraction was lyophilized to obtain 1.5 mg of a complex of okadaic acid and OVA (OA-OVA for short) as an immunogen.

An antigen for analysis was prepared by the following procedure.

The foregoing procedure for preparing the immunogen was repeated except that 1 mg of 1-ethyl-3-(2-dimethylaminopropyl)carbodiimide hydrochloride (EDPC) was used instead of CMEC and bovine serum albumin (BSA) was used instead of OVA. As a result, 6 mg of a complex of okadaic acid and BSA (OA-BSA for short) was obtained as an antigen for analysis.

EXAMPLE 2

Preparation of a hybridoma capable of producing a monoclonal antibody to okadaic acids:

(a) Immunization of mice and preparation of spleen lymphocytes

One milliliter of a solution of 400 micrograms of OA-OVA (immunogen) in PBS and 1 ml of complete Freund's adjuvant were fully mixed to form an emulsion. 0.5 ml of the resulting emulsion was intraperitoneally administered to BALB/c mice female, 8 weeks old).

Two weeks and four weeks after this first immunization, 0.5 ml of an emulsion prepared as above was also administered intraperitoneally to the mice.

Two weeks later, a solution of 100 micrograms of the above antigen in 0.5 ml of PBS was administered intravenously via to the tail vein of the mice as a final immunization.

On the third day after the final immunization, the spleen was removed from the immunized mice, and washed in a Petri dish holding RPMI 1640 (a solution of a powdery medium for culturing lymphocytes in distilled water). It was transferred to another petri dish holding RPMI 1640 medium and disintegrated by a pincette.

The resulting floating lymphocytes were suspended in RPMI 1640 medium, centrifuged (rotating speed 1000 rpm; time 5 minutes), and again suspended in a RPMI 1640 medium to obtain mouse spleen lymphocytes for use in cell fusion.

(b) Cell fusion $5 \times 10^7$ 8-Azaguanine-resistant mouse myeloma cells (X63-Ag.653; 653) in the logarithmic growth phase and $2.5 \times 10^8$ spleen lymphocytes prepared above were put in a 50 ml plastic conical centrifugation tube and mixed, and centrifuged (rotating speed 1400 rpm; time 6 minutes). The supernatant was removed. The centrifugation tube was lightly tapped to disintegrate the pellets.

While vigorously shaking the pellets, conical tube, 1 ml of a 50% aqueous solution of PEG 4000 at 37° C. was added over 1 minute. One minute later, RPMI 1640 medium at 37° C. was gradually added until its amount reached 10 ml. The mixture was centrifuged at 800 rpm for 6 minutes at room temperature, and the supernatant was removed by suction.

The centrifugation tube was lightly tapped to disintegrate the pellets, and the pellets were suspended in 150 ml of a HAT medium (RPMI 1640 medium containing $1 \times 10^{-4}$ M hipoxanthine, $4 \times 10^{-7}$ M aminopterine, $1.6 \times 10^{-5}$ M thymidine and 20% fetal bovine serum). The suspension was poured into the wells of a 96-well culture plate at a rate of 100 microliters per well, and incubated in a $CO_2$ incubator (5% $CO_2$, 95% air, 37° C., humidity 100%)

(c) Selection of a hybridoma

In the course of 2 to 4 weeks after the start of the culturing in (b) above, it was determined by the following ELISA method whether the culture supernatants in those wells of the culture plate in which cell proliferation was observed contained an antibody to OA.

The OA-BSA solution as an analytical antigen prepared in Example 1 (5 micrograms/ml, dissolved in 0.05 M carbonate buffer having a pH of 9.8) was poured at a rate of 50 microliters per well to analytical wells of a 96-well U-bottomed ELISA plate, and left to stand overnight at 4° C. (by this treatment, OA-BSA adsorbed to the surface of each of the analytical well).

The analytical wells of the ELISA plate were washed with a washing solution (PBS containing 0.05% Tween 20), and a 0.5% BSA solution (dissolved in PBS) was poured into the analytical wells at a rate of 100 microliters per well, and left to stand at room temperature for 2 hour. The analytical wells were washed with a washing solution. The culture supernatants in those wells of the culture plate which are described above were added to the analytical wells at a rate of 50 microliters per well, and left to stand at room temperature for 2 hours. As a negative control, a supernatant obtained by similarly culturing a mixture of mouse spleen cells and mouse myeloma cells before fusion was used, whereas the serum of the mice used in cell fusion in this invention was diluted to 100-fold and used as a positive control.

The analytical wells were washed with a washing solution, and a solution of an alkaline phosphataselabelled antibody to mouse immunoglobulins was added to the analytical wells at a rate of 50 microliters, and left to stand at room temperature for 1 hour. The analytical wells were again washed, and a solution of p-nitrophenylphosphate disodium salt hexahydrate (1 mg/ml) was added to the analytical wells at a rate of 100 microliters. The absorbance at 405 nm of the wells was measured by using a spectrophotometer for microplates.

As a result, in seven out of 888 wells in the culture plate, the production of an antibody to OA was observed.

An inhibition test using OA was conducted on the 7 wells in which the antibody was produced. The test was done by the same procedure as in the above ELISA except that instead of the supernatant poured into the wells, a solution prepared by adding 1 microgram per well of OA to the supernatant was used.

Three wells were found to contain an antibody inhibited by OA. It was thus determined that in these three wells, a hybridoma existed which produced an antibody which reacted with OA.

(d) Cloning of the hybridoma

The hybridoma cells in the three wells in which antibody production was confirmed in step (c) above were cloned in a RPMI 1640 medium containing 20% fetal bovine serum by a single cell manipulation method (the method in which one hybridoma cell is put in one well under an inverted microscope).

A 96-well culture plate was used, and a BALB/c mouse thymus cell suspension ($10^8$ cells/ml was used as feeder cells. In the culturing, 100 microliters of the thymus cell suspension was used per hybridoma cell per well.

Beginning with about 10 days after the start of the culturing, the supernatant was taken from the wells of the culture plate observed as a single colony, and screened for antibody-producing wells by the ELISA method using OA-BSA as the analytical antigen [the same method as in step [(c)]. With respect to the supernatants in which antibody production was observed, their reactivity with $DTX_1$, an okadaic acid-like diarrhetic shellfish poison was examined.

Three cell strains which reacted both with OA and $DTX_1$ were obtained, and re-cloned.

The resulting strains were named OA-1 strain, OA-2 strain (FERM No. 1491) and OA-3 strain, and the monoclonal antibodies produced by these cell strains were named OA-1, OA-2 and OA-3.

The classes, subclasses and L-chain types of the monoclonal antibodies contained in the culture supernatants of these three strains were determined by the following measuring test I, and their reactivity with various antigens was examined by the following measuring test II.

Measuring test I

Determination of classes and subclasses of monoclonal antibodies to okadaic acids The classes and subclasses of the immunoglobulins produced by the OA-1 strain, OA-2 strain and OA-3 strain were determined by the same ELISA method as in step (c) using a solution of a peroxidase-labelled antibody specific to each class or subclass of the mouse antibody (an antibody labelled with horseradish peroxidase to $IgG_1$, $IgG_{2a}$, $IgG_{2b}$, $IgG_3$, IgM, IgA, κ-type L-chains or λ-type L-chains), and the Ouchterlony gel diffusion method using an antiserum specific to each class and subclass of the mouse antibody (antibody $IgG_1$, $IgG_{2a}$, $IgG_{2b}$, $IgG_3$, IgM, IgA, κ-type L-chains or λ-type L-chains).

The results showed that the monoclonal antibody (OA-1) produced by the OA-1 strain is an immunoglobulin belonging to IgA having -type L-chains, and the monoclonal antibodies (OA-2 and OA-3) produced by the OA-2 and OA-3 are immunoglobulins belonging to $IgG_1$ having -type L-chains.

Measuring test II

Reactivity of the monoclonal antibodies to OA acids with other shellfish poisons:

The reactivities of monoclonal antibodies OA-1, OA-2 and OA-3 with other shellfish poisons such as pectenotoxin-1 ($PTX_1$) and yessotoxin (YTX) were examined by the same ELISA method as in step (c) described above (except that the amount of the reagent used in assaying was doubled, and instead of the culture supernatant of the hybridoma, a mixture of 25 microliters of a monoclonal antibody solution and 25 microliters of a shellfish poison solution diluted to various concentrations with a washing solution was used).

The reactivities of these antibodies with OA, $DTX_1$, $PTX_1$ and YTX are shown in Table 1 in terms of the reactivity ratios to OA.

TABLE 1

| Shellfish poison | OA-1 | OA-2 | OA-3 |
| --- | --- | --- | --- |
| OA | 1 | 1 | 1 |
| $DTX_1$ | 1.07 | 0.87 | 0.74 |
| $PTX_1$ | <0.0004 | <0.0003 | <0.0003 |
| YTX | 0.006 | 0.006 | 0.004 |

EXAMPLE 3

Production of a monoclonal antibody to okadaic acids by culturing in a flask

Cultured cells of the OA-2 strain obtained by culturing in an RPMI 1640 medium containing 5% fetal bovine serum were transferred to 10 ml of an RPMI 1640 medium (not containing fetal bovine serum) and cultured till they were soon to die.

A monoclonal antibody to okadaic acids (OA-1) was contained in an amount of 38 micrograms/ml (measured by a single radial immunodiffusion method) in the culture supernatant which was obtained by centrifugation (rotating) at 3000 rpm for 5 minutes).

EXAMPLE 4

Production of a monoclonal antibody to okadaic acids in the abdominal cavity of mice To obtain a large amount of a monoclonal antibody to okadaic acids, cells of the OA-1 strain were cultured in the abdominal cavity of the mouse.

$5 \times 10^6$ cells of the OA-1 strain floating in RPMI 1640 were administered intraperitoneally to BALB/c mice (female, 6 weeks old; 0.5 ml of pristane had been administered intraperitoneally two weeks before).

The body weight of the mice began to increase markedly in about 1 week, and in two weeks, ascites (7.6 ml/mouse) was taken from the mice and centrifuged at 3000 rpm for 5 minutes to obtain an ascites supernatant.

The monoclonal antibody (OA-1) to okadaic acids was contained in an amount of 8.5 mg/ml (measured by the single radial immunodiffusion method) in the ascites supernatant.

EXAMPLE 5

Production of a monoclonal antibody to okadaic acids in the abdominal cavity of mice $10^7$ cells of the OA-2 strain floating in phosphate buffer were intraperitoneally administered to BALB/c mice male, 8 weeks old; 0.5 ml of pristane had been administered intraperitoneally two weeks before) and cultured to produce a monoclonal antibody (OA-2).

The body weight of the mice began to increase markedly in about 1 week, and in one to three weeks, ascites was taken from the mice. The antibody titer of the resulting monoclonal antibody was $10^6$ to $10^8$.

The monoclonal antibody was isolated and purified from the ascites by the following procedure. The ascites was dialyzed against Tris-HCl buffer (pH 7.4) and charged onto a DEAE-cellulose column equilibrated with the same buffer. Fractions which passed through the column were salted out with 50% saturated ammonium sulfate. The resulting precipitate was dissolved in PBS and dialyzed. The purity of the resulting monoclonal antibody to okadaic acids was found to be high as a result of analysis by SDS polyacrylamide gel electrophoresis.

EXAMPLE 6

Preparation of a reagent for assaying okadaic acids

The purified monoclonal antibody (OA-2) described in Example 5 was labelled by a known enzyme labelling method to prepare an assay reagent for assaying okadaic acids.

Horseraddish peroxidase 7.32 mg) was dissolved in 1 ml of distilled water, and 200 microliters of 0.1 M sodium periodate was added. The mixture was allowed to stand for 30 minutes at room temperature. The resulting enzyme solution was dialyzed overnight at 4° C. against 1 mM acetate buffer (pH 4.5). Then, 100 microliters of 0.2 M sodium carbonate buffer (pH 9.5) was added to adjust the pH of the solution to 9.5. Separately, 8 mg of the monoclonal antibody OA-2 dissolved in 0.1 M phosphate buffer (pH 7.4) was dialyzed overnight at 4° C. using 0.01 M sodium carbonate buffer (pH 9.5).

The resulting peroxidase solution and monoclonal antibody solution were mixed and left to stand at room temperature for 2.5 hours. To the reaction mixture was added 100 to 200 microliters of 0.4% by weight sodium borohydride. The resulting peroxidase-labelled monoclonal antibody was fully dialyzed at 4° C. against PBS and either as such or after lyophilization, used as an assay reagent for assaying okadaic acids.

EXAMPLE 7

Preparation of a calibration curve for OA

OA-BSA (a complex of okadaic acid and BSA, 5 micrograms/ml) was allowed to stand overnight at 4° C. on a 96-well flat-bottomed immunoplate (made by Nunc Company) and fixed. To avoid non-specific adsorption of the antibody on the plate, PBS containing 10% bovine serum was put in the wells of the plate, and left to stand at room temperature for 30 minutes. The blocking solution was discarded, and the plate was washed with a fresh supply of a washing solution (PBS containing 0.05% Tween 20). The okadaic acid assaying reagent (50 microliters) and a standard OA solution prepared by using 50 microliters of a 45% aqueous solution of methanol [(0–45 ng)/50 microliters] were added simultaneously to each of the wells, and left to stand (A) at room temperature for 5 minutes, or (B) at 37° C. for 30 minutes. Subsequently, a substrate solution (a mixture of o-phenylenediamine and $H_2O_2$) was put in the wells at a rate of 100 microliters per well, and while shutting off light with an aluminum foil, left to stand (A) at room temperature for 3 minutes or (B) at 37° C. for 15 minutes. Finally, 2N sulfuric acid was added at a rate of 50 microliters per well to stop the enzyme reaction. After the stopping of the reaction, the absorbance of the reaction mixture at 492 nm was measured by using a microplate photometer.

The results obtained by the procedure (A) and those obtained by the procedure (B) are shown in FIG. 1 (the absorbance at an OA concentration of 0 g/ml was taken as 100%). The amount of OA could be measured to the order of several ng by any of the procedures (A) and (B).

EXAMPLE 8

Test for recovering OA

The digestive glands were taken out from scallops on the market, and crushed by a mixer. A 90% aqueous solution of methanol (12.5 ml; 2.5 times the amount of the crushed mass) was added to 5 g of the crushed mass. The mixture was further subjected to a mixer for one minute to extract OA.

The extract was filtered through filter paper No. 1 of Toyo Filter Paper, and the filtrate was diluted (1:1) with pure water to provide a 45% aqueous solution of methanol. Using this as a sample, a test for recovering OA was conducted in accordance with Example 7. In this experiment, a known amount of OA was added to the sample in advance, and the amount of OA added was later measured. As shown in Table 2, the calculated amount of OA added to the sample, and the amount of OA measured showed a substantial agreement with each other (the absorbance at an OA concentration of 0 g/ml was taken as 100%).

TABLE 2

| Concentration of OA (ng/ml) | | Recovery |
| --- | --- | --- |
| Calculated | Measured | (%) |
| 20 | 18 | 90 |
| 100 | 100 | 100 |
| 300 | 320 | 107 |

We claim:
1. A monoclonal antibody to okadaic acids.
2. The monoclonal antibody of claim 1 in which the okadaic acids are represented by the following formula

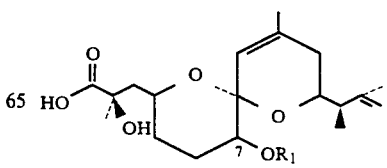

-continued

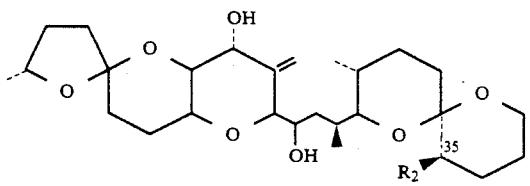

wherein $R_1$ represents a hydrogen atom or an acyl group, and $R_2$ represents a hydrogen atom or a methyl group.

3. An assay reagent for assaying okadaic acids comprising an enzyme-labelled monoclonal antibody which specifically binds to okadaic acids.

4. A monoclonal antibody to okadaic acids labelled with an enzyme which is selected from the group consisting of peroxidase, alkaline phosphatase, beta-galactosidase, catalase, glucose oxidase, lactic acid oxidase, alcohol oxidase and monoamine oxidase.

5. A method of measuring okadaic acid, which comprises contacting a sample containing okadaic acid or a sample likely to contain okadaic acid with an acid an enzyme-labelled monoclonal antibody which specifically binds to okadaic acid under competitive reaction conditions and detecting an amount of the monoclonal antibody bound to okadaic acid in the sample.

* * * * *